United States Patent
Gao et al.

(10) Patent No.: US 12,311,137 B2
(45) Date of Patent: May 27, 2025

(54) HYDROGEL MICRONEEDLE PATCH BASED ON THREE-DIMENSIONAL FRAMEWORK STRUCTURE, AND PREPARATION METHOD AND APPLICATION THEREOF

(71) Applicants: TECHNICAL INSTITUTE OF PHYSICS AND CHEMISTRY OF THE CHINESE ACADEMY OF SCIENCES, Beijing (CN); Beijing CAS Microneedle Technology Ltd., Beijing (CN)

(72) Inventors: Yunhua Gao, Beijing (CN); Mengzhen Xing, Beijing (CN)

(73) Assignees: Technical institute of physics and chemistry of the chinese academy of sciences, Beijing (CN); Beijing CAS Microneedle Technology Ltd., Beijing (CN)

( * ) Notice: Subject to any disclaimer, the term of this patent is extended or adjusted under 35 U.S.C. 154(b) by 0 days.

(21) Appl. No.: 18/661,731

(22) Filed: May 13, 2024

(65) Prior Publication Data

US 2024/0293653 A1 Sep. 5, 2024

Related U.S. Application Data

(63) Continuation of application No. PCT/CN2023/098758, filed on Jun. 7, 2023.

(30) Foreign Application Priority Data

Jun. 9, 2022 (CN) .......................... 202210645460.4

(51) Int. Cl.
*A61L 31/04* (2006.01)
*A61L 31/14* (2006.01)
*A61M 37/00* (2006.01)

(52) U.S. Cl.
CPC ....... *A61M 37/0015* (2013.01); *A61L 31/048* (2013.01); *A61L 31/145* (2013.01);
(Continued)

(58) Field of Classification Search
CPC .. A61M 2037/0023; A61M 2037/0046; A61M 2037/0053; A61M 2037/0061; A61M 37/0015; A61K 9/0021
See application file for complete search history.

(56) References Cited

U.S. PATENT DOCUMENTS

2002/0082543 A1* 6/2002 Park .................. A61M 37/0015
604/20
2009/0043279 A1* 2/2009 Kaspar ................ A61K 9/0021
604/506

(Continued)

FOREIGN PATENT DOCUMENTS

CN 113164376 A 7/2021

*Primary Examiner* — Kevin C Sirmons
*Assistant Examiner* — William R Frehe

(57) ABSTRACT

A hydrogel microneedle patch based on a three-dimensional framework structure is provided and includes a hydrogel microneedle. A raw material of the hydrogel microneedle includes polyvinyl alcohol and aqueous dispersion of acrylic resin. the hydrogel microneedle is obtained by uniformly mixing and molding of the aqueous dispersion of acrylic resin and the polyvinyl alcohol. The hydrogel microneedle patch has good strength, excellent swelling property and puncture property. In addition, a preparation method and an application of the hydrogel microneedle patch are also provided.

3 Claims, 6 Drawing Sheets

(52) U.S. Cl.
CPC ............ *A61M 2037/0023* (2013.01); *A61M 2037/0046* (2013.01); *A61M 2037/0053* (2013.01)

(56) References Cited

U.S. PATENT DOCUMENTS

| | | | |
|---|---|---|---|
| 2017/0087199 A1* | 3/2017 | Patron | A61K 31/381 |
| 2018/0369136 A1* | 12/2018 | Narayan | A61K 9/0021 |
| 2021/0346665 A1* | 11/2021 | Xu | A61K 45/06 |
| 2023/0051189 A1* | 2/2023 | Liu | A61M 37/0076 |
| 2024/0245754 A1* | 7/2024 | Yin | A61M 37/0015 |
| 2024/0366923 A1* | 11/2024 | Cabiri | A61K 9/0065 |

* cited by examiner

HYDROGEL MICRONEEDLE PATCH BASED ON THREE-DIMENSIONAL FRAMEWORK STRUCTURE, AND PREPARATION METHOD AND APPLICATION THEREOF

TECHNICAL FIELD

The disclosure relates to the technical field of transdermal delivery, and particularly to a hydrogel microneedle patch based on a three-dimensional framework structure, and a preparation method and an application thereof.

BACKGROUND

A hydrogel microneedle refers to a microneedle technology, which can achieve needle expansion in a body fluid environment by absorbing interstitial skin fluid and thus promote drugs release, but a matrix of the hydrogel microneedle is insoluble and can be taken out completely after drugs release. It has the following advantages: drugs release can be controllable by adjusting a cross-linking strength of a hydrogel network; after use of the hydrogel microneedle, there is no residual matrix and excipients in a corresponding body; and biological safety is higher. It was first reported in 2010 that the hydrogel microneedle can rapidly absorb tissue fluid to expand after acting on a skin, and can maintain an open state of skin microchannels for a long time, which makes its application fields more extensive. Specifically, the hydrogel microneedle can be applied in the following four fields. 1. The hydrogel microneedle can replace a solid silicon microneedle and can break the skin stratum corneum barrier. 2. The hydrogel microneedle can be combined with traditional drugs loaded transdermal preparations to improve an effective transdermal drug delivery efficiency of conventional skin preparations such as water, emulsion, patch and gel. 3. The hydrogel microneedle can be used as a drug carrier to carry active ingredients directly, which has the characteristics of large drug load and controllable drug release rate by controlling the internal crosslinking degree of the system. 4. The hydrogel microneedle can be used for rapid detection and extraction of biomolecules in interstitial fluid, with obvious efficiency and cost advantages. Compared with the solid microneedles of metal and monocrystalline silicon, the hydrogel microneedles have better material toughness, and there is no need to worry about the risks of tip fracture and residue in the skin during use. Compared to a dissolving microneedle, the hydrogel microneedles are insoluble and non-degradable in a body fluid environment, so there is no need to worry about the accumulation of macromolecular polymers in the body due to long-term use, which makes their use more convenient, safe and reliable.

The reported hydrogel microneedles are mostly cross-linked microneedles obtained by hydrogen bonding between polymer chains or esterification reaction. Polyvinyl alcohol (PVA) hydrogel microneedles were prepared by the Jin Tuo research group of Shanghai Jiaotong University through a repeated freezing and thawing process of freezing at a temperature of −20° C. and thawing at a temperature of 4° C., which can achieve effective delivery of biomacromolecule drugs. However, the preparation of the microneedles requires the cross-linking process of repeated freezing and thawing cycles, which is time-consuming and cumbersome, and is not suitable for industrial preparation. Donnelly's group at Queen's University has been working on the cross-linking of poly(methyl vinyl ether-alt-maleic anhydride) copolymer (PMVE/MA) and polyethylene glycol (PEG) into ester under a higher temperature of 80° C. or microwave conditions, and has made super hydrogel microneedles with a dissolution rate of 1,600%, which are suitable for percutaneous delivery of drugs of different molecular weights. However, the cross-linking process of microneedles has to react at 80° C. for 24 hours or in a microwave environment for 8 hours, which makes the microneedle preparation efficiency low and is not conducive to the batch production. In addition, the high-temperature preparation conditions can easily lead to the destruction of the drug stability, which limits the scope of the applicable drugs.

SUMMARY

A first purpose of the disclosure is to provide a hydrogel microneedle patch based on a three-dimensional framework structure, the hydrogel microneedle patch utilizes the three-dimensional framework structure of aqueous dispersion of acrylic resin to enclose a gel formed by polyvinyl alcohol with poorer cohesion, and the polyvinyl alcohol gives the aqueous dispersion of acrylic resin with no mechanical strength a certain degree of mechanical strength, such that the hydrogel microneedle patch has both excellent swelling and piercing properties.

A second purpose of the disclosure is to provide a preparation method of the hydrogel microneedle patch based on the three-dimensional framework structure. The preparation method can produce hydrogel microneedles under the condition of natural drying and needle forming, overcomes the limitation of cross-linking conditions in the related art, and has the advantages of a simpler preparation process, convenient operation and a faster needle forming speed.

A third purpose of the disclosure is to provide an application method of the hydrogel microneedle patch based on the three-dimensional framework structure.

To achieve the first purpose mentioned above, the disclosure adopts the following technical solution as follows.

A hydrogel microneedle patch based on a three-dimensional framework structure includes a hydrogel microneedle, a raw material of the hydrogel microneedle includes polyvinyl alcohol and water dispersion of acrylic resin, and the hydrogel microneedle is obtained by uniformly mixing and molding of the aqueous dispersion of acrylic resin and the polyvinyl alcohol. In the hydrogel microneedle patch, aqueous dispersion of acrylic resin is configured to, as the three-dimensional framework structure, enclose a gel formed by the polyvinyl alcohol.

In an embodiment, a mass ratio of the polyvinyl alcohol to the aqueous dispersion of acrylic resin is in a range of 5-50:0.1-10.

In an embodiment, it is understood that the hydrogel microneedle includes needle tips and a needle base, the needle tips and the needle base can be integrated as a single-piece structure, or can be formed as separate structures.

In an embodiment, the hydrogel microneedle further includes a backing, and the backing is combined with the needle base.

In an embodiment, functional additives and active substances can also be added into the hydrogel microneedle patch according to actual needs. In a specific embodiment, the backing of the hydrogel microneedle patch is a hydrocolloid patch with a hollow structure, the hydrocolloid patch plays the role of fixing the microneedle to the skin, and the active substances can be added into the hollow structure such that the active substances can be in directly contact with the needle base. In another specific embodiment, the backing of the hydrogel microneedle patch is an adhesive sponge backing, the adhesive sponge backing has good adhesion and drug loading capability, and can load the active substances.

In an embodiment, the polyvinyl alcohol has a high alcoholysis degree and the alcoholysis degree of the polyvinyl alcohol is above 98%.

The aqueous dispersion of acrylic resin is an aqueous system, which uses water as dispersion medium, and is obtained by dispersing solid spherical/spherical-like particles or semi-solid spherical/spherical-like particles with a particle size in a range of 100-1000 nanometers (nm) in the water, which undergoes limited swelling in a biological media, and forms a dense three-dimensional framework structure. The polyvinyl alcohol with the high alcoholysis degree and high molecular weight is a swelling hydrogel material. In the process of drying microneedle solution to form microneedles, hydrogen bonding forces are formed within and between polyvinyl alcohol molecules. After encountering water, a part of the polyvinyl alcohol and water molecules form hydrogen bonds, which weakens the hydrogen bonding effect within the polyvinyl alcohol molecules themselves, thereby leading the cohesion reduction of the microneedles. After swelling in water, the microneedles are transformed to a state of gel and cannot be completely removed from the skin. Based on the properties of the above two materials, in the disclosure, the two materials are evenly mixed, the framework structure of the aqueous dispersion of acrylic resin is used to enclose the polyvinyl alcohol gel with poorer cohesion, and the polyvinyl alcohol endows the aqueous dispersion of acrylic resin without mechanical strength with a certain mechanical strength, as such, the prepared hydrogel microneedles of the disclosure has both excellent swelling property and puncture property.

In an embodiment, the aqueous dispersion of acrylic resin includes one or more selected from the group consisting of acrylic resin, emulsifier, preservative, alkalizer, organic solvent and purified water.

In an embodiment, the acrylic resin includes one or more selected from the group consisting of ethyl acrylate, methyl methacrylate, methacryloxyethyltrimethyl ammonium chloride, methylacrylate and methacrylic acid.

In an embodiment, the emulsifier includes one or more selected from the group consisting of diethylene glycol monooctadecyl ether, polyethylene glycol trimethylnonyl ether, sodium dodecyl sulfate and polysorbate 80 (also referred to as Tween 80).

In an embodiment, the preservative includes one or more selected from the group consisting of sorbic acid, benzoic acid, dehydroacetic acid and paraben.

In an embodiment, the alkalizer includes one or more selected from the group consisting of sodium hydroxide, potassium hydroxide, sodium bicarbonate and ethanolamine.

In an embodiment, the organic solvent includes one or more selected from the group consisting of ethyl alcohol and butyleneglycol.

In an embodiment, in the aqueous dispersion of acrylic resin, the acrylic resin include one or more selected from the group consisting of a copolymer of ethyl acrylate and methyl methacrylate with a molar ratio of 2:1, a copolymer of methacrylic acid, methylacrylate and methyl methacrylate with a molar ratio of 1:1:1, a copolymer of ethyl acrylate, methyl methacrylate and methacryloxyethyltrimethyl ammonium chloride with a molar ratio of 1:2:0.1, a copolymer of ethyl acrylate, methyl methacrylate and methacryloxyethyltrimethyl ammonium chloride with a molar ratio of 1:2:0.2, and a copolymer of methacrylic acid and ethyl acrylate with a molar ratio of 1:1.

In an embodiment, the hydrogel microneedle further includes a pore-forming agent.

In an embodiment, the pore-forming agent is located in one or more selected from the group consisting of the polyvinyl alcohol and the aqueous dispersion of acrylic resin.

In an embodiment, a mass percentage of the pore-forming agent in the hydrogel microneedle is in a range of 0.1-10 weight percent (wt %).

In an embodiment, the pore-forming agent includes one or more selected from the group consisting of polyvinylpyrrolidone, calcium phosphate dibasic, sodium bicarbonate, sodium carbonate, trehalose, fructose, sorbitol, mannitol, xylitol, galactose, magnesium chloride, calcium chloride and zinc chloride.

The pore-forming agent is a small molecule substance that can be dissolved from the three-dimensional framework structure, which helps to expand internal network gaps of the microneedles, forming a larger drug delivery space. For high molecular weight drugs such as proteins, larger channels are conducive to rapid drug delivery. On the one hand, the degree of the cross-linking of the polyvinyl alcohol is controlled to control a density of the three-dimensional network, thereby controlling a drug delivery rate. On the other hand, the control of drug delivery with different properties can be achieved by controlling the use of the pore-forming agent. In addition, during infrared radiation cross-linking process, as the degree of the cross-linking of PVA increases, an edge of the microneedle can be warped. When the polyvinylpyrrolidone is added, it can not only act as the pore-forming agent, but also improve the flatness of the microneedle.

To achieve the second purpose mentioned above, the disclosure adopts the following technical solution as follows.

A preparation method of the hydrogel microneedle patch based on the three-dimensional framework structure includes the following steps:

preparing an aqueous solution of the polyvinyl alcohol;
dissolving the aqueous solution of the polyvinyl alcohol at a target temperature to obtain a dissolved solution of the polyvinyl alcohol, after the dissolving, adding aqueous dispersion of acrylic resin into the dissolved solution of the polyvinyl alcohol and performing mixing to obtain a mixed aqueous solution, then removing bubbles of the mixed aqueous solution, and performing molding and crosslinking on the mixed aqueous solution after removing bubbles to thereby obtain the hydrogel microneedle patch.

In an embodiment, the cross-linking includes one of infrared radiation cross-linking, physical freeze-thaw cross-linking, chemical agent cross-linking, annealing treatment cross-linking, microwave-assisted cross-linking and radiating cross-linking.

In an embodiment, an infrared wavelength for the infrared radiation cross-linking is in a range of 1000-5000 nanometers (nm).

In an embodiment, a mass percentage of the polyvinyl alcohol in the mixed aqueous solution is in a range of 5-50 wt %.

In an embodiment, a mass percentage of the aqueous dispersion of acrylic resin in the mixed aqueous solution is in a range of 0.1-10 wt %.

To achieve the third purpose mentioned above, the disclosure provides an application method of the hydrogel microneedle patch, and the application method incudes performing a transdermal delivery of an active substance through the hydrogel microneedle patch.

In an embodiment, the transdermal delivery includes one of using the hydrogel microneedle patch as a transdermal enhancer, combining the hydrogel microneedle patch combined with a drug-loaded patch, and directing loading a drug through the hydrogel microneedle patch.

The disclosure further provides another application method of the hydrogel microneedle patch, which includes using the hydrogel microneedle patch to extract biomolecules from interstitial fluid of skin.

In an embodiment, the hydrogel microneedle patch can play the role of skin pore-formation, act as a transdermal enhancer, and promote percutaneous penetration of the active substance. The specific usage method of the hydrogel microneedle patch can refer to the existing usage methods of solid microneedles of metals and monocrystalline silicon, which will not be repeated here.

In an embodiment, the hydrogel microneedle patch can be used in combination with the solution, lotion, cream, gel and a patch loaded with the active substance. The specific use method can refer to the use method of the existing hydrogel microneedle patch, which will not be repeated here.

In an embodiment, the hydrogel microneedle patch can directly be loaded with the active substance to achieve intradermal drug delivery.

In an embodiment, the hydrogel microneedle patch can absorb tissue fluid, thereby realizing the extraction of biomolecules in the interstitial fluid of skin.

In an embodiment, the active substance includes one or more selected from the group consisting of a small molecule drug, a traditional Chinese drug extract, a peptide, proteins, and a vaccine.

The beneficial effects of the disclosure are as follow.

In the hydrogel microneedle patch, the framework structure of the aqueous dispersion of acrylic resin is used to enclose the polyvinyl alcohol gel with poor cohesion, and the polyvinyl alcohol gives the aqueous dispersion of acrylic resin without mechanical strength a certain strength, so as to prepare the hydrogel microneedle with both excellent swelling property and puncture property. In the preparation method of the hydrogel microneedle patch, because the specific aqueous dispersion of acrylic resin and the polyvinyl alcohol are selected, it is possible to adopt a new cross-linking method, and the hydrogel microneedles can be made under the condition of natural drying to form the needle, which has the advantages of simple microneedle preparation process, convenient operation and fast needle forming speed.

BRIEF DESCRIPTION OF DRAWINGS

The following will provide further detailed explanations of the specific embodiments of the disclosure in conjunction with the attached drawings.

DETAILED DESCRIPTION OF EMBODIMENTS

In order to provide a clearer explanation of the disclosure, further explanation will be given below in conjunction with specific embodiments and attached drawings. Similar components in the diagram are represented by the same diagram markings. Those skilled in the art should understand that the specific description below is explanatory rather than restrictive and should not limit the scope of protection of the disclosure.

Embodiment 1 Preparation and Puncture Effect of Hydrogel Microneedle Patch

Figure 1:
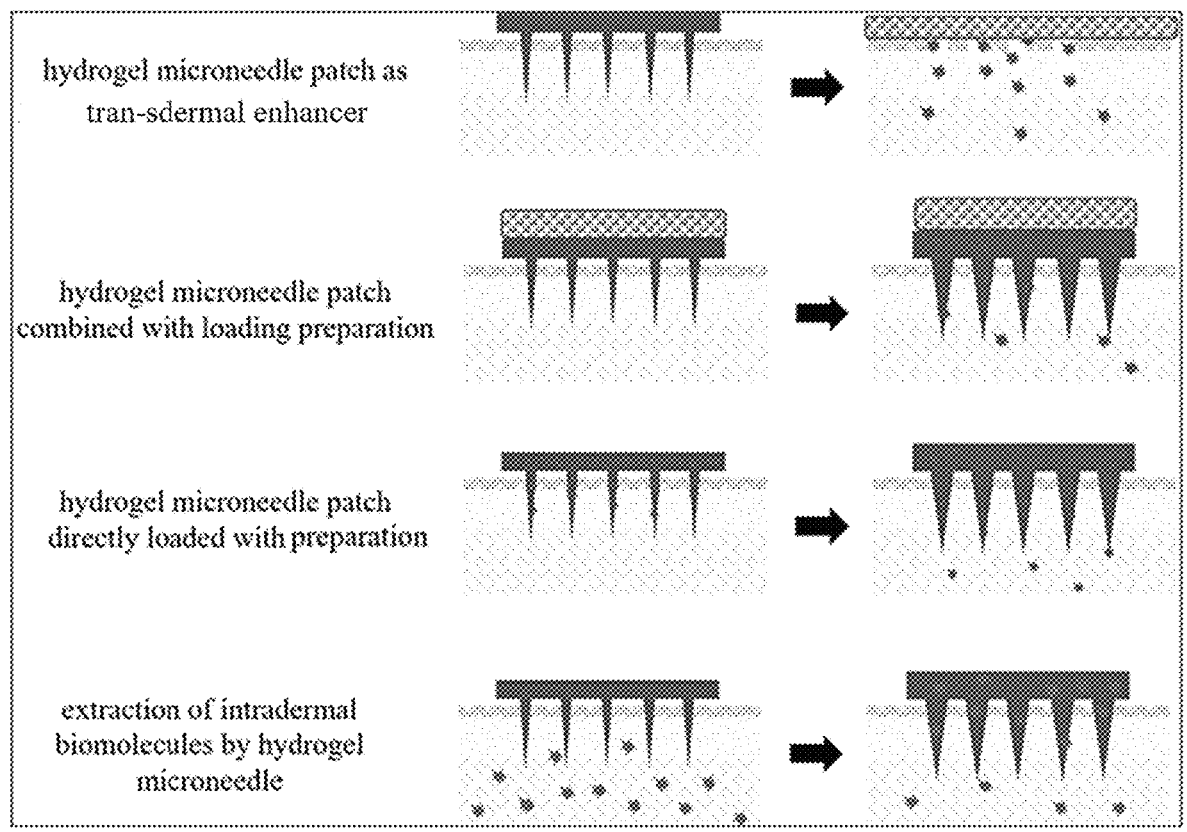
FIG. 1 illustrates a schematic diagram of four application modes of hydrogel microneedle patches of the disclosure.
Figure 2:
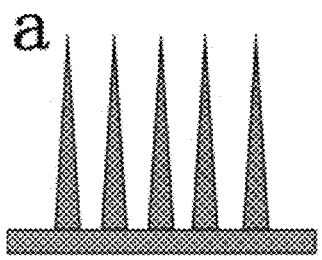
FIG. 2 illustrates an external structural diagram of the hydrogel microneedle patch of the disclosure.
Figure 3:
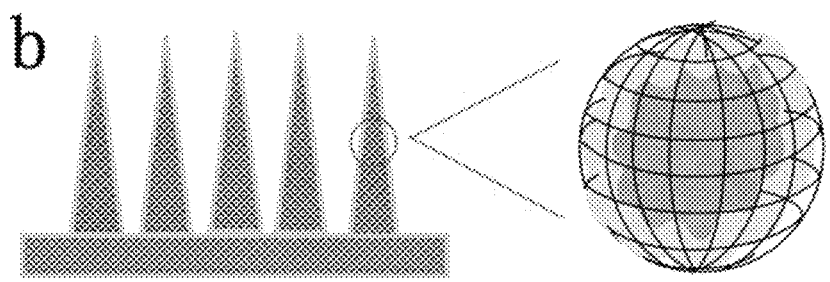
FIG. 3 illustrates an external structure and an internal structure of a swelled hydrogel microneedle patch after absorption of body fluid of the disclosure.

In the embodiment 1, a hydrogel microneedle patch is prepared through the following steps. A measuring cylinder is used to take 17 millimeters (ml) of purified water. 2.2 grams (g) of polyvinyl alcohol are add into the purified water to obtain a first mixed solution, then the mixed solution is placed into an oven at a temperature of 90° C. to dissolve, thereby obtaining a polyvinyl alcohol solution. 0.8 g of aqueous dispersion of acrylic resin (i.e., a copolymer of ethyl acrylate and methyl methacrylate with a molar ratio of 2:1) is added into the polyvinyl alcohol solution, followed by evenly stirring to obtain a mixed aqueous solution, in which, a mass percentage of the polyvinyl alcohol in the mixed aqueous solution is 11 wt %, and a mass percentage of the aqueous dispersion of acrylic resin in the mixed aqueous solution is of 4 wt %. Bubbles of the mixed aqueous solution are removed. The microneedle is prepared by a mold method, specifically, the mixed aqueous solution is added into a mold of the microneedle, and the hydrogel microneedle patch is obtained after the microneedle is dried to form a film (i.e. patch). A structure diagram of the hydrogel microneedle patch is shown in FIG. 2, and an external structure and an internal structure of a swelled hydrogel microneedle patch after absorption of body fluid are shown in FIG. 3.

Figure 4:
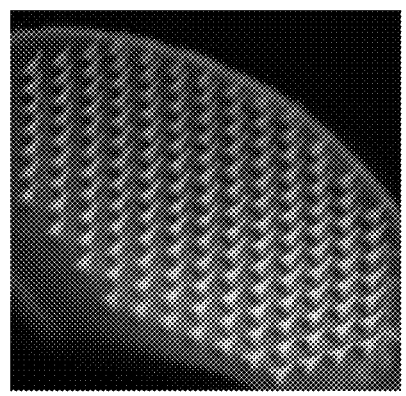
FIG. 4 illustrates a microscope topography of the hydrogel microneedle patch from a stereomicroscope in an embodiment 1 of the disclosure.
Figure 5:
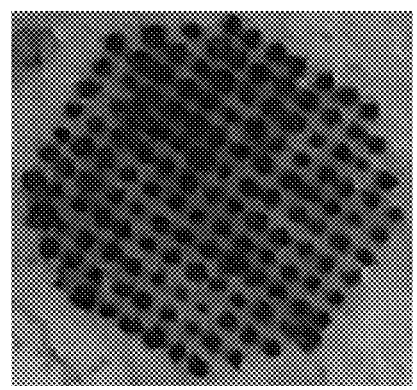
FIG. 5 illustrates a skin puncture diagram of the hydrogel microneedle patch in the embodiment 1 of the disclosure.

The hydrogel microneedle patch is placed under a stereomicroscope to observe a morphology of the microneedle, and the skin puncture performance of the microneedle is tested through pig skin puncture test in vitro. A specific operation is as follows: frozen and off-body skin of pig, depilated, with a thickness of 600 micrometers (μm), from a refrigerator working at −20° C. is taken to thaw naturally at room temperature. After the thawing, a surgical knife is used to cut the skin of pig with an area 1 centimeter (cm)×1 cm to obtain a skin block, a filter paper is used to absorb moisture from a side of stratum corneum of the skin block, and followed by laying the skin block flat on a surface of a silicone mold with the side of stratum corneum facing upward. A needle inserter (with a pressure of 20 newtons per square centimeter ($N/cm^2$)) is used to apply the microneedle to the skin for 20 seconds (s), followed by removing the microneedle, and then the skin block is stained with 4 milligrams per milliliter (mg/ml) of a trypan blue dye for 30 minutes (min). After the staining, the excess trypan blue dye on the surface of the skin block is wiped off with a cotton swab, a formation of a complete pinhole array on the skin block can be observed. The results are as shown in FIGS. 4 and 5, which shows that the hydrogel microneedle prepared in this embodiment has complete needle body morphology, sharp and full needle tips, and have good skin puncture properties.

Embodiment 2 Preparation of Hydrogel
Microneedle Patch Containing Trehalose as
Pore-Forming Agent In the embodiment 2, a hydrogel microneedle patch is prepared through the following steps. A measuring cylinder is used to take 16.2 ml of purified water, 2.4 g of polyvinyl alcohol are add into the purified water to obtain a first mixed solution, then the first mixed solution is placed into an oven at a temperature of 90° C. to dissolve, thereby obtaining a polyvinyl alcohol solution. 1.4 g of aqueous dispersion of acrylic resin (i.e., a copolymer of ethyl acrylate and methyl methacrylate with a molar ratio of 2:1) is added into the polyvinyl alcohol solution, followed by evenly stirring to obtain a mixed aqueous solution, in which a mass percentage of the polyvinyl alcohol in the mixed aqueous solution is 12 wt %, and a mass percentage of the aqueous dispersion of acrylic resin in the mixed aqueous solution is of 7 wt %. Bubbles of the mixed aqueous solution are removed.

Figure 6:
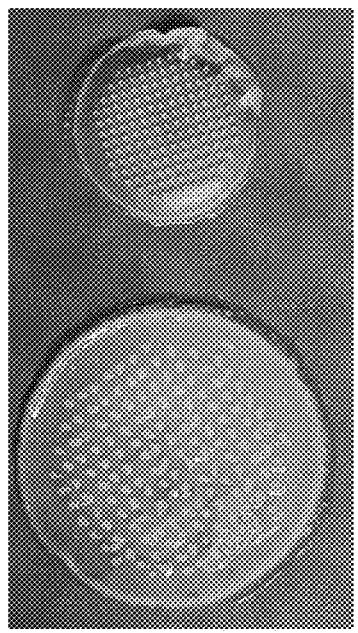
FIG. 6 illustrates a comparison diagram of morphologies before (left) and after (right) swelling of the hydrogel microneedle patch in an embodiment 2 of the disclosure.

The microneedle is prepared by the mold method, the mixed aqueous solution is added into a mold of the microneedle, and the hydrogel microneedle patch is obtained after the microneedles are dried to form a film. After the drying, the film is placed in a phosphate buffer solution with a pondus hydrogenii (pH) of 7.4 to swell at 37° C. for 8 hours, followed by taking out, observing and comparing morphological changes of microneedles before and after the swelling. As shown in FIG. 6, the results show that after 8 hours of the swelling, the water absorption volume of the microneedle significantly increases, but the microstructure such as the needle tip remains intact, indicating that the microneedle has a good swelling property.

Embodiments 3-14 Preparation of Hydrogel
Microneedle Patch Containing Other Pore-Forming
Agents The microneedle solution is prepared according to the microneedle preparation method in the embodiment 2 and combined with the hydrogel microneedle prescription containing different types of pore-forming agents in Table 1, thereby obtaining a series of the hydrogel microneedle patches. By observing whether the integrity of the microneedle tip with each prescription is maintained after the swelling for 8 hours at 37° C. in the phosphate buffer solution with pH of 7.4, then whether the microneedle has the swelling property is determined. The results are shown in the Table 1, indicating that each hydrogel microneedle with each prescription has a good swelling property in vitro.

TABLE 1

Prescription of hydrogel microneedles with different pore-forming agents and swelling properties of the prepared microneedles

| Embodiment | Content of polyvinyl alcohol (wt %) | Types and content of water dispersion of acrylic resin (wt %) | Types and content of pore-forming agent (wt %) | Content of ultral water (wt %) | Swelling property | Swelling rate (%) |
|---|---|---|---|---|---|---|
| 3 | 30 | a copolymer of ethyl acrylate and methyl methacrylate (2:1) with a molar ratio of 2:1 (1) | Polyvinylpyrrolidone (10) | 59 | Yes | 493.21 ± 46.32 |
| 4 | 28 | a copolymer of methacrylic acid, methylacrylate and methyl methacrylate with a molar ratio of 1:1:1 (3) | Fructose (9) | 60 | Yes | 467.42 ± 24.65 |
| 5 | 26 | a copolymer of ethyl acrylate, methyl methacrylate and methacryloxyethyltrimethyl ammonium chloride with a molar ratio of 1:2:0.1 (5) | Galactose (8) | 61 | Yes | 412.89 ± 39.01 |

TABLE 1-continued

Prescription of hydrogel microneedles with different pore-forming agents and swelling properties of the prepared microneedles

| Embodiment | Content of polyvinyl alcohol (wt %) | Types and content of water dispersion of acrylic resin (wt %) | Types and content of pore-forming agent (wt %) | Content of ultral water (wt %) | Swelling property | Swelling rate (%) |
|---|---|---|---|---|---|---|
| 6 | 24 | a copolymer of ethyl acrylate, methyl methacrylate and methacryloxyethyltrimethyl ammonium chloride with a molar ratio of 1:2:0.2 (7) | Mannitol (7) | 62 | Yes | 369.43 ± 25.66 |
| 7 | 22 | a copolymer of methacrylic acid and ethyl acrylate with a molar ratio of 1:1 (9) | Xylitol (6) | 63 | Yes | 374.90 ± 32.88 |
| 8 | 20 | a copolymer of ethyl acrylate and methyl methacrylate with a molar ratio of 2:1 (NM30D) (10) | Sorbitol (5) | 65 | Yes | 309.71 ± 29.03 |
| 9 | 18 | a copolymer of ethyl acrylate and methyl methacrylate with a molar ratio of 2:1 (8) | Calcium perphosphate (4) | 70 | Yes | 464.23 ± 56.01 |
| 10 | 16 | a copolymer of methacrylic acid, methylacrylate and methyl methacrylate with a molar ratio of 1:1:1 (6) | Sodium bicarbonate (3) | 75 | Yes | 477.21 ± 32.22 |
| 11 | 15 | a copolymer of ethyl acrylate, methyl methacrylate and methacryloxyethyltrimethyl ammonium chloride with a molar ratio of 1:2:0.1 (4) | Sodium carbonate (2) | 79 | Yes | 512.06 ± 42.82 |
| 12 | 14 | a copolymer of ethyl acrylate, methyl methacrylate and methacryloxyethyltrimethyl ammonium chloride with a molar ratio of 1:2:0.2 (2) | Magnesium chloride (1) | 83 | Yes | 444.52 ± 33.61 |
| 13 | 12 | a copolymer of methacrylic acid and ethyl acrylate with a molar ratio of 1:1 (6) | Calcium chloride (0.5) | 81.5 | Yes | 309.45 ± 72.31 |
| 14 | 10 | a copolymer of ethyl acrylate and methyl methacrylate with a molar ratio of 2:1 (5) | Zinc chloride (0.2) | 84.8 | Yes | 342.76 ± 49.76 |

Embodiment 15 Preparation of Hydrogel Microneedle Patch Through Infrared Radiation Cross-Linking In the embodiment 15, a hydrogel microneedle patch is prepared through the following steps. A measuring cylinder is used to take 16.2 ml of purified water, 2.8 g of polyvinyl alcohol are add into the purified water to obtain a first mixed solution, then the first mixed solution is placed into an oven at a temperature of 90° C. to dissolve, thereby obtaining a polyvinyl alcohol solution. 1 g of water dispersion of acrylic resin (i.e., a copolymer of methacrylic acid, methylacrylate and methyl methacrylate with a molar ratio of 1:1:1) is added into the polyvinyl alcohol solution, followed by evenly stirring to obtain a mixed aqueous solution, in which a mass percentage of the polyvinyl alcohol in the mixed aqueous solution is 14 wt %, and a mass percentage of the aqueous dispersion of acrylic resin in the mixed aqueous solution is of 5 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. The film is placed under an infrared lamp with an infrared wavelength in a range of 2400-3500 nm to be radiated at 70° C. for 1 minute to promote cross-linking. The microneedles having not undergone infrared radiation cross-linking and undergone infrared radiation cross-linking are taken to weigh separately, after the weighing, the microneedles having not undergone infrared radiation cross-linking and undergone infrared radiation cross-linking are placed in a phosphate buffer solution with a pH of 7.4 to swell at 37° C. for 8 hours, followed by taking out and absorbing moisture from the surface of the microneedles by using the filter paper for further weighing, and a weighing formula is: swelling rate=(weight of microneedles after swelling−weight of microneedles before swelling)/weight of microneedles before swelling×100%. The weighing formula is used to calculate the effect of the infrared radiation cross-linking on the swelling rate of microneedles. As shown in Table 2, the results indicate that the swelling rate of the microneedles by the infrared radiation cross-linking is significantly reduced, which indicates that infrared radiation can further enhance the cohesion between polyvinyl alcohol molecules, form more hydrogen bonds between polyvinyl alcohol molecules, and thus reduce the swelling rate of the microneedles. In addition, on the basis of the network formed by the original PVA and the aqueous dispersion of acrylic resin, it is found that PVA itself can achieve its self-crosslinking through infrared radiation. Although the network framework of PVA in the aqueous dispersion can be controlled to ensure that the microneedle still has a complete needle shape after the swelling. In fact, due to the gel nature of PVA, a small amount of PVA still dissolve into the solvent medium. When the dissolution of PVA is expected to further control, the cross-linking between PVA molecules can be further strengthened, thereby achieving higher cross-linking degree.

TABLE 2

Comparison of swelling rate of hydrogel microneedle patches having not undergone and undergone infrared radiation cross-linking

| Group | Weight before swelling (g) | Weight after swelling (g) | Swelling rate (%) | Average (%) |
|---|---|---|---|---|
| Uncross-linked group | 0.00312 | 0.01684 | 439.74 | 395.01 |
|  | 0.00333 | 0.01517 | 355.56 |  |
|  | 0.00351 | 0.01719 | 389.74 |  |
| Infrared cross-linking group | 0.00283 | 0.01307 | 361.84 | 318.93 |
|  | 0.00359 | 0.01434 | 299.44 |  |
|  | 0.00334 | 0.01321 | 295.51 |  |

Embodiment 16 Preparation of Hydrogel Microneedle Patch Through Physical Freeze-Thaw Cross-Linking In the embodiment 16, a hydrogel microneedle patch is prepared through the following steps. A measuring cylinder is used to take 16.8 ml of purified water, 3 g of polyvinyl alcohol are add into the purified water to obtain a first mixed solution, then the mixed solution is placed into an oven at a temperature of 90° C. to dissolve, thereby obtaining a polyvinyl alcohol solution. 0.2 g of aqueous dispersion of acrylic resin (i.e., a copolymer of methacrylic acid, methylacrylate and methyl methacrylate with a molar ratio of 1:1:1) are added into the polyvinyl alcohol solution, followed by evenly stirring to obtain a mixed aqueous solution, in which a mass percentage of the polyvinyl alcohol in the mixed aqueous solution is 15 wt %, and a mass percentage of the aqueous dispersion of acrylic resin in the mixed aqueous solution is of 1 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. The mold with the film is placed in a refrigerator at −20° C. for freezing treatment for 8 h, and then placed in a refrigerator at 4° C. for melting treatment for 8 h. After repeating the freezing treatment and the melting treatment twice, cross-linked hydrogel microneedle patches are obtained. The microneedles having not undergone the freeze-thaw cross-linking and undergone the freeze-thaw cross-linking are taken to weigh separately, after the weighing, the microneedles having not undergone the freeze-thaw cross-linking and undergone the freeze-thaw cross-linking are placed in a phosphate buffer solution with a pH of 7.4 to swell at 37° C. for 8 hours, followed by taking out and absorbing moisture from the surface of the microneedles by using the filter paper for further weighing, and a weighing formula is: swelling rate=(weight of microneedles after swelling-weight of microneedles before swelling)/weight of microneedles before swelling×100%. The weighing formula is used to calculate the effect of the freeze-thaw cross-linking on the swelling rate of microneedles. As shown in Table 3, the results indicate that the swelling rate of the microneedles by the freeze-thaw cross-linking is significantly reduced, which indicate that repeated freeze-thaw cycles can further enhance the cohesion between polyvinyl alcohol molecules, form more hydrogen bonds between the polyvinyl alcohol molecules, and thus reduce the swelling rate of the microneedles. In addition, on the basis of the network formed by the original PVA and the aqueous dispersion of acrylic resin, it is found that PVA itself can achieve its self-crosslinking through the repeated freeze-thaw cycles. Although the network framework of PVA in the aqueous dispersion can be controlled to ensure that the microneedle still has a complete needle shape after the swelling. In fact, due to the gel nature of PVA, a small amount of PVA still dissolve into the solvent medium. When the dissolution of PVA is expected to further control, the cross-linking between PVA molecules can be further strengthened, thereby achieving higher cross-linking degree.

TABLE 3

Comparison of swelling rate of hydrogel microneedle patches having not undergone and undergone freeze-thaw cross-linking

| Group | Weight before swelling (g) | Weight after swelling (g) | Swelling rate (%) | Average (%) |
|---|---|---|---|---|
| Uncross-linked group | 0.00324 | 0.01713 | 428.70 | 426.27 |
|  | 0.00334 | 0.01678 | 402.40 |  |
|  | 0.00327 | 0.01791 | 447.71 |  |
| Freeze-thaw cross-linking group | 0.00292 | 0.01328 | 354.79 | 323.11 |
|  | 0.00317 | 0.01290 | 306.94 |  |
|  | 0.00329 | 0.01341 | 307.60 |  |

Embodiment 17 Preparation of Hydrogel Microneedle Patch Through Chemical Agent Cross-Linking In the embodiment 17, a hydrogel microneedle patch is prepared through the following steps. A measuring cylinder is used to take 16.2 ml of purified water, 2.4 g of polyvinyl alcohol are add into the purified water to obtain a first mixed solution, then the mixed solution is placed into an oven at a temperature of 90° C. to dissolve, thereby obtaining a polyvinyl alcohol solution. 1.2 g of aqueous dispersion of acrylic resin (i.e., a copolymer of methacrylic acid, methylacrylate and methyl methacrylate with a molar ratio of 1:1:1) and a chemical cross-linking agent of 0.2 g of glutaraldehyde are added into the polyvinyl alcohol solution, followed by evenly stirring to obtain a mixed aqueous solution, in which a mass percentage of the polyvinyl alcohol in the mixed aqueous solution is 14 wt %, and a mass percentage of the aqueous dispersion of acrylic resin in the mixed aqueous solution is of 5 wt %. Bubbles of the mixed aqueous solution are removed. The microneedle is prepared by the mold method, the mixed aqueous solution is added into a mold of the microneedle, and the hydrogel microneedle patch through the chemical agent cross-linking is obtained after the microneedles are dried to form a film. The microneedles having not undergone the chemical agent cross-linking and undergone the chemical agent cross-linking are taken to weigh separately, after the weighing, the microneedles having not undergone the chemical agent cross-linking and undergone the chemical agent cross-linking are placed in a phosphate buffer solution with a pH of 7.4 to swell at 37° C. for 8 hours, followed by taking out and absorbing moisture from the surface of the microneedles by using the filter paper for further weighing, and a weighing formula is: swelling rate=(weight of microneedles after swelling-weight of microneedles before swelling)/weight of microneedles before swelling×100%. The weighing formula is used to calculate the effect of the chemical agent cross-linking on the swelling rate of microneedles. As shown in Table 4, the results show that the swelling rate of the microneedles through the chemical agent cross-linking is significantly reduced, indicating that the chemical cross-linking agent can form chemical bonds with hydroxyl groups of the polyvinyl alcohol, and increasing the degree of cross-linking in the system, thereby reducing the swelling rate of the microneedles. On the basis of the network formed by the original PVA and aqueous dispersion of acrylic resin, it is found that PVA itself can be self-crosslinked through the chemical cross-linking agents. Although the network framework of PVA in the aqueous dispersion can be controlled to ensure that the microneedle still has a complete needle shape after the swelling. In fact, due to the gel nature of PVA, a small amount of PVA still dissolve into the solvent medium. When the dissolution of PVA is expected to further control, the cross-linking between PVA molecules can be further strengthened, thereby achieving higher cross-linking degree.

TABLE 4

Comparison of swelling rate of hydrogel microneedle patches having not undergone and undergone chemical agent cross-linking

| Group | Weight before swelling (g) | Weight after swelling (g) | Swelling rate (%) | Average (%) |
|---|---|---|---|---|
| Uncross-linked group | 0.00341 | 0.01742 | 410.85 | 418.63 |
|  | 0.00332 | 0.01786 | 437.95 |  |
|  | 0.00367 | 0.01861 | 407.08 |  |
| Chemical agent cross-linking group | 0.00305 | 0.01102 | 261.31 | 253.47 |
|  | 0.00324 | 0.01219 | 276.23 |  |
|  | 0.00341 | 0.01101 | 222.87 |  |

Embodiment 18 Preparation of Hydrogel Microneedle Patch Through Microwave-Assisted Cross-Linking In the embodiment 18, a hydrogel microneedle patch is prepared through the following steps. A measuring cylinder is used to take 15.9 ml of purified water, 4 g of polyvinyl alcohol are add into the purified water to obtain a first mixed solution, then the first mixed solution is placed into an oven at a temperature of 90° C. to dissolve, thereby obtaining a polyvinyl alcohol solution. 0.1 g of aqueous dispersion of acrylic resin (i.e., a copolymer of methacrylic acid, methylacrylate and methyl methacrylate with a molar ratio of 1:1:1) are added into the polyvinyl alcohol solution, followed by evenly stirring to obtain a mixed aqueous solution, in which a mass percentage of the polyvinyl alcohol in the mixed aqueous solution is 14 wt %, and a mass percentage of the aqueous dispersion of acrylic resin in the mixed aqueous solution is of 5 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. After forming the film, the hydrogel microneedle patch is placed in a microwave oven to be microwaved for 10 minutes, thereby promoting cross-linking. The microneedles having not undergone the chemical agent cross-linking and undergone the chemical agent cross-linking are taken to weigh separately, after the weighing, the microneedles having not undergone the chemical agent cross-linking and undergone the chemical agent cross-linking are placed in a phosphate buffer solution with a pH of 7.4 to swell at 37° C. for 8 hours, followed by taking out and absorbing moisture from the surface of the microneedles by using the filter paper for further weighing, and a weighing formula is: swelling rate-(weight of microneedles after swelling–weight of microneedles before swelling)/weight of microneedles before swelling×100%. The weighing formula is used to calculate the effect of the microwave-assisted cross-linking on the swelling rate of microneedles. As shown in Table 5, the results indicate that the swelling rate of the microneedles by the microwave-assisted cross-linked is significantly reduced, which indicates that microwave-assisted cross-linking can further enhance the cohesion between polyvinyl alcohol molecules, form more hydrogen bonds between polyvinyl alcohol molecules, and thus reduce the swelling rate of the microneedles. In addition, on the basis of the network formed by the original PVA and the aqueous dispersion of acrylic resin, it is found that PVA itself can achieve its self-crosslinking through the microwave-assisted cross-linking. Although the network framework of PVA in the aqueous dispersion can be controlled to ensure that the microneedle still has a complete needle shape after the swelling. In fact, due to the gel nature of PVA, a small amount of PVA still dissolve into the solvent medium. When the dissolution of PVA is expected to further control, the cross-linking between PVA molecules can be further strengthened, thereby achieving higher cross-linking degree.

TABLE 5

Comparison of swelling rate of hydrogel microneedle patches having not undergone and undergone microwave-assisted cross-linking

| Group | Weight before swelling (g) | Weight after swelling (g) | Swelling rate (%) | Average (%) |
|---|---|---|---|---|
| Uncross-linked group | 0.00361 | 0.01825 | 405.54 | 407.75 |
|  | 0.00383 | 0.01867 | 387.47 |  |
|  | 0.00377 | 0.01999 | 430.24 |  |
| Microwave-assisted cross-linking group | 0.00395 | 0.01699 | 330.13 | 310.78 |
|  | 0.00362 | 0.01432 | 295.58 |  |
|  | 0.00377 | 0.01533 | 306.63 |  |

Embodiment 19 Preparation of Hydrogel Microneedle Patch Through Radiating Cross-Linking In the embodiment 15, a hydrogel microneedle patch is prepared through the following steps. A measuring cylinder is used to take 15.2 ml of purified water, 3.2 g of polyvinyl alcohol are add into the purified water to obtain a first mixed solution, then the first mixed solution is placed into an oven at a temperature of 90° C. to dissolve, thereby obtaining a polyvinyl alcohol solution. 1.6 g of aqueous dispersion of acrylic resin (i.e., a copolymer of methacrylic acid, methylacrylate and methyl methacrylate with a molar ratio of 1:1:1) are added into the polyvinyl alcohol solution, followed by evenly stirring to obtain a mixed aqueous solution, in which a mass percentage of the polyvinyl alcohol in the mixed aqueous solution is 16 wt %, and a mass percentage of the aqueous dispersion of acrylic resin in the mixed aqueous solution is of 8 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. After forming the film, the hydrogel microneedle patch is placed under an electron beam to perform the radiation treatment for 20 minutes, thereby promoting cross-linking. The microneedles having not undergone the radiating cross-linking and undergone the radiating cross-linking are taken to weigh separately, after the weighing, the microneedles having not undergone the radiating cross-linking and undergone the radiating cross-linking are placed in a phosphate buffer solution with a pH of 7.4 to swell at 37° C. for 8 hours, followed by taking out and absorbing moisture from the surface of the microneedles by using the filter paper for further weighing, and a weighing formula is: swelling rate= (weight of microneedles after swelling−weight of microneedles before swelling)/weight of microneedles before swelling×100%. The weighing formula is used to calculate the effect of the radiating cross-linking on the swelling rate of microneedles. As shown in Table 6, the results show that the swelling rate of the microneedles through the radiating cross-linking is significantly reduced, indicating that the radiation cross-linking can cause the formation of hydroxyl radicals by the secondary carbon and tertiary carbon in polyvinyl alcohol molecular chains. After removing the radiation, the free radicals undergo a double-base coupling reaction to form chemical bond cross-linking, thereby reducing the swelling rate of the microneedles. In addition, on the basis of the network formed by the original PVA and the aqueous dispersion of acrylic resin, it is found that PVA itself can achieve its self-crosslinking through the radiating cross-linking. Although the network framework of PVA in the aqueous dispersion can be controlled to ensure that the microneedle still has a complete needle shape after the swelling. In fact, due to the gel nature of PVA, a small amount of PVA still dissolve into the solvent medium. When the dissolution of PVA is expected to further control, the cross-linking between PVA molecules can be further strengthened, thereby achieving higher cross-linking degree.

TABLE 6

Comparison of swelling rate of hydrogel microneedle patches having not undergone and undergone radiating cross-linking

| Group | Weight before swelling (g) | Weight after swelling (g) | Swelling rate (%) | Average (%) |
|---|---|---|---|---|
| Uncross-linked group | 0.00354 | 0.01784 | 403.95 | 406.95 |
| | 0.00338 | 0.016757 | 395.77 | |
| | 0.00369 | 0.01923 | 421.14 | |
| Radiating cross-linking group | 0.00378 | 0.01678 | 343.92 | 347.81 |
| | 0.00344 | 0.01645 | 378.20 | |
| | 0.00361 | 0.01521 | 321.33 | |

Figure 7:
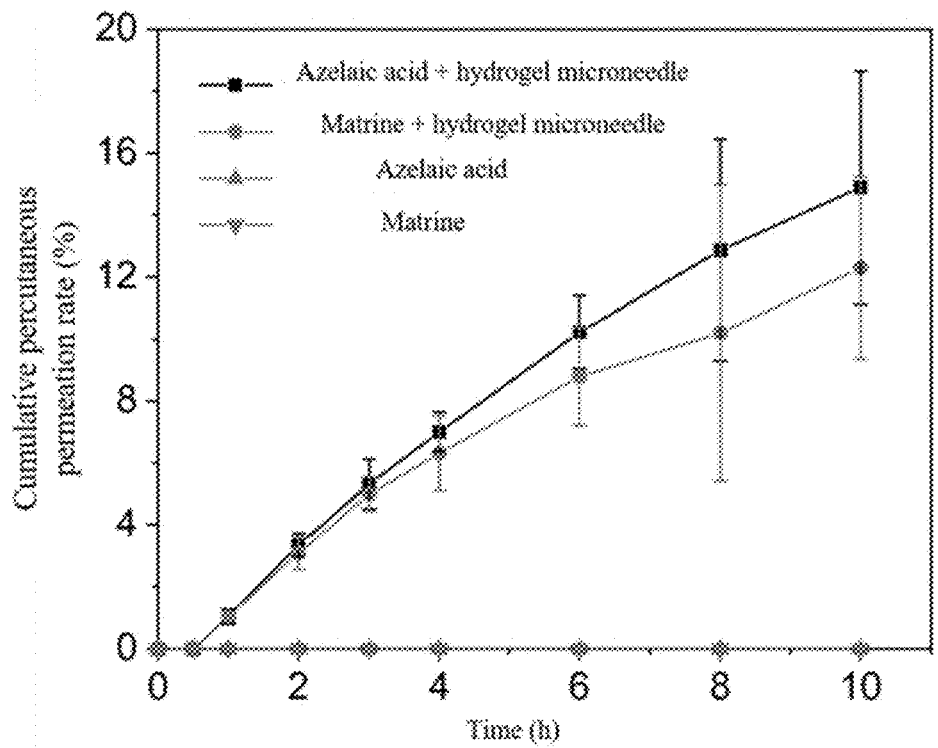
FIG. 7 illustrates cumulative percutaneous permeabilities of azelaic acid and matrine after pores are formed on a skin surface through a hydrogel microneedle in an embodiment 20 of the disclosure.

Embodiment 20 Percutaneous Permeability of Hydrogel Microneedle Patch as Transdermal Enhancer to Aqueous Solution of Active Ingredients In the embodiment 20, a hydrogel microneedle patch is prepared through the following steps. A measuring cylinder is used to take 16.4 ml of purified water, 2.4 g of polyvinyl alcohol are add into the purified water to obtain a first mixed solution, then the mixed solution is placed into an oven at a temperature of 90° C. to dissolve, thereby obtaining a polyvinyl alcohol solution. 1.2 g of aqueous dispersion of acrylic resin (i.e., a copolymer of ethyl acrylate and methyl methacrylate with a molar ratio of 2:1) are added into the polyvinyl alcohol solution, followed by evenly stirring to obtain a mixed aqueous solution, in which a mass percentage of the polyvinyl alcohol in the mixed aqueous solution is 12 wt %, and a mass percentage of the aqueous dispersion of acrylic resin in the mixed aqueous solution is of 6 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. An aqueous solution containing 1% azelaic acid and 1.3% matrine is prepared as an active ingredient solution. The hydrogel microneedle patch is applied to the cuticle side of the off-body skin of pig, the hydrogel microneedle is pressed for 20 seconds with a self-made needle inserter (with a pressure of 20 N/cm$^2$), followed by taking off the hydrogel microneedle patch, and fixing the off-body skin of pig in a transdermal cup. 100 ml of the active ingredient solution is added to a side of a drug delivery pool of the transdermal cup, and followed by automatically sampling with a fully automatic transdermal device. The drug content in a collection pool is analyzed by using a high-performance liquid chromatography device to calculate the cumulative transdermal transmittance of the drug. As shown in FIG. 7, the results show that the use of hydrogel microneedle patch as a transdermal enhancer can effectively open the drug delivery microchannel on the surface of skin and promote the percutaneous penetration of the active ingredient solution. In a continuous 10-hour percutaneous penetration test in vitro, the cumulative delivery rates of azelaic acid and matrine are 14.90±3.77% and 12.30±2.95%, respectively. In addition, a blank control group is set to drip the same volume of active ingredient solution onto a cuticle side of untreated and intact skin, and the untreated and intact skin is fixed on the transdermal cup in the same way for transdermal permeability test in vitro. The results show that the azelaic acid and matrine in the blank control group could not effectively penetrate the cuticle barrier of the untreated and intact skin into the receiving cell within 10 hours, indicating that the hydrogel microneedle patch could effectively play the role of skin pore formation and promote the transdermal delivery of active ingredient aqueous solution.

Figure 8:
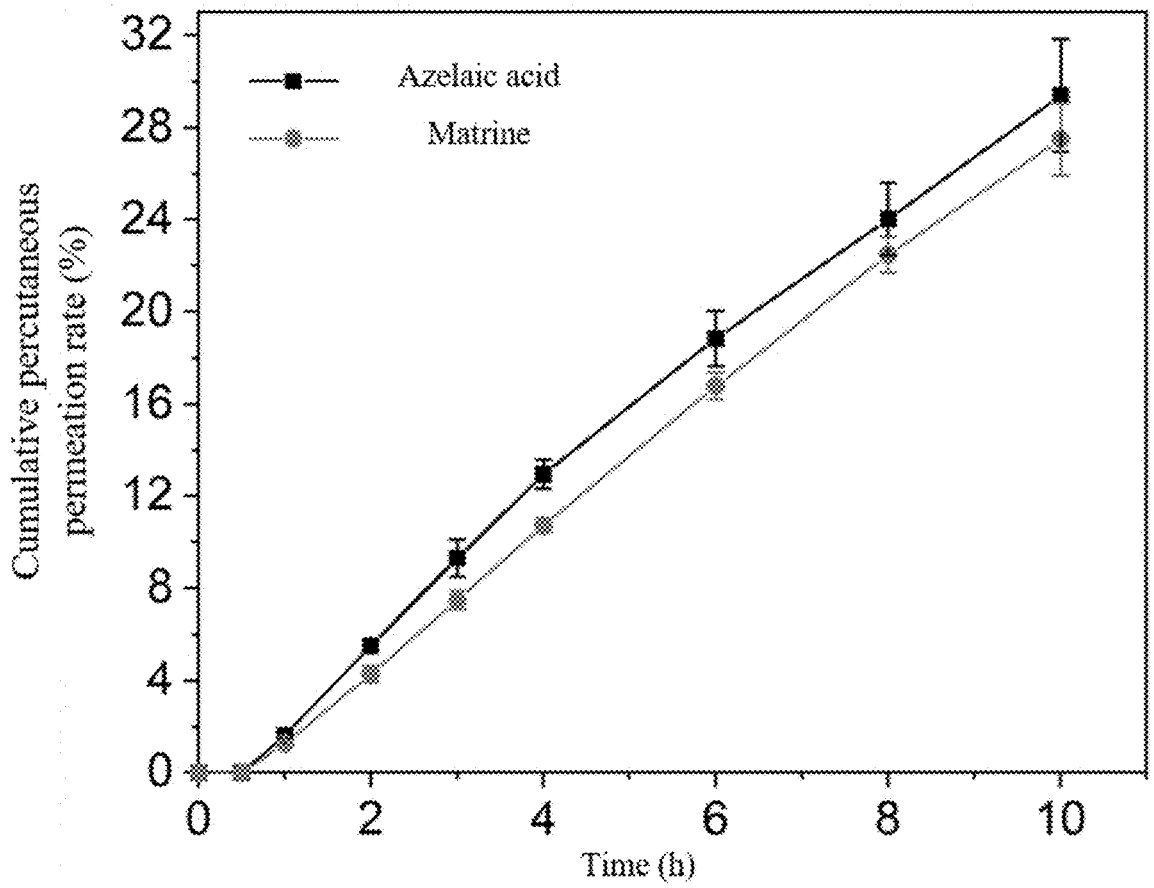
FIG. 8 illustrates cumulative percutaneous permeabilities of azelaic acid and matrine after applying a combination of azelaic acid aqueous solution and a hydrogel microneedle patch on a skin surface and applying a combination of matrine aqueous solution and a hydrogel microneedle patch on a skin surface in an embodiment 21 of the disclosure.

Embodiment 21 Percutaneous Permeability of Hydrogel Microneedle Patch Combined with Aqueous Solution of Active Ingredients In the embodiment 21, a hydrogel microneedle patch is prepared through the following steps. A measuring cylinder is used to take 16.4 ml of purified water, 2.4 g of polyvinyl alcohol are add into the purified water to obtain a first mixed solution, then the mixed solution is placed into an oven at a temperature of 90° C. to dissolve, thereby obtaining a polyvinyl alcohol solution. 1.2 g of aqueous dispersion of acrylic resin (i.e., a copolymer of ethyl acrylate and methyl methacrylate with a molar ratio of 2:1) are added into the polyvinyl alcohol solution, followed by evenly stirring to obtain a mixed aqueous solution, in which a mass percentage of the polyvinyl alcohol in the mixed aqueous solution is 12 wt %, and a mass percentage of the aqueous dispersion of acrylic resin in the mixed aqueous solution is of 6 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. An aqueous solution containing 1% azelaic acid and 1.3% matrine is prepared as an active ingredient solution. The hydrogel microneedle patch is applied to the cuticle side of the off-body skin of pig, the hydrogel microneedle is pressed for 20 seconds with a self-made needle inserter (with a pressure of 20 N/cm$^2$) to make the microneedle insert into the off-body skin, and followed by fixing the off-body skin of pig with the microneedles in a transdermal cup. 100 ml of the active ingredient solution is added to a side of a drug delivery pool of the transdermal cup, and followed by automatically sampling with a fully automatic transdermal device. The drug content in a collection pool is analyzed by using a high-performance liquid chromatography device to calculate the cumulative transdermal transmittance of the drug. As shown in FIG. 8, the results show that when the hydrogel microneedle patch is used together with the aqueous solution of the active ingredient, effective drug permeation can be achieved. After continuous 10-hours applying, the cumulative permeation rates of azelaic acid and matrine are 29.42±2.43% and 27.51±1.57% respectively, which makes the water-soluble drug with poor percutaneous permeability have good permeation efficiency in the field of percutaneous delivery.

Figure 9:
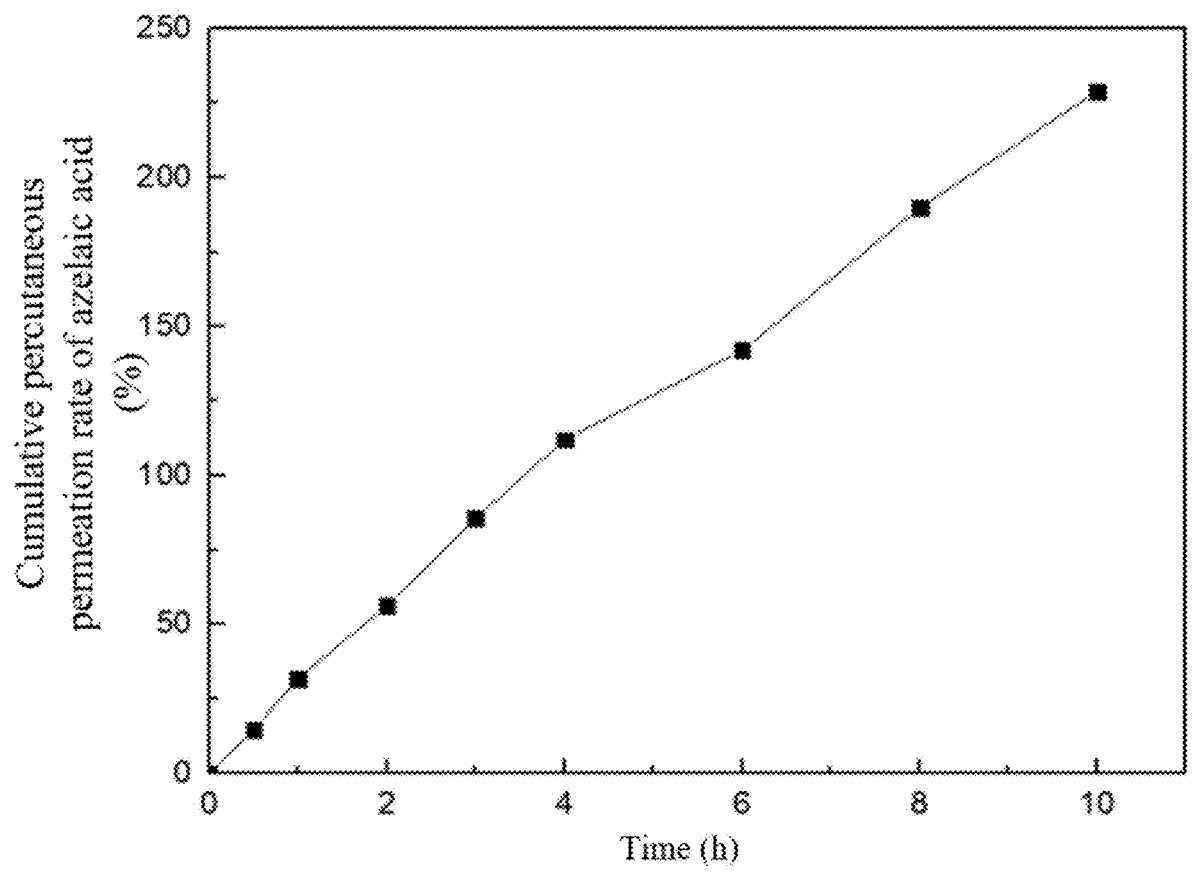
FIG. 9 illustrates a cumulative percutaneous permeability of azelaic acid after applying a combination of the 15% azelaic acid gel (also referred to as azelaic acid 15% gel) available in the market and a hydrogel microneedle patch on a skin surface in an embodiment 22 of the disclosure.

Embodiment 22 Percutaneous Permeability of Hydrogel Microneedle Patch Combined with Gel of Active Ingredient In the embodiment 22, a hydrogel microneedle patch is prepared through the following steps. A measuring cylinder is used to take 16.4 ml of purified water, 2.4 g of polyvinyl alcohol are add into the purified water to obtain a first mixed solution, then the mixed solution is placed into an oven at a temperature of 90° C. to dissolve, thereby obtaining a polyvinyl alcohol solution. 1.2 g of aqueous dispersion of acrylic resin (i.e., a copolymer of ethyl acrylate and methyl methacrylate with a molar ratio of 2:1) are added into the polyvinyl alcohol solution, followed by evenly stirring to obtain a mixed aqueous solution, in which a mass percentage of the polyvinyl alcohol in the mixed aqueous solution is 14 wt %, and a mass percentage of the aqueous dispersion of acrylic resin in the mixed aqueous solution is of 5 wt %. Bubbles of the mixed aqueous solution are removed. The microneedle is prepared by the mold method, the mixed aqueous solution is added into a mold of the microneedle, and the hydrogel microneedle patch is obtained after the microneedles are dried to form a film. An aqueous solution containing 1% azelaic acid and 1.3% matrine is prepared as an active ingredient solution. The hydrogel microneedle patch is applied to the cuticle side of the off-body skin of pig, the hydrogel microneedle is pressed for 20 seconds with a self-made needle inserter (with a pressure of 20 N/cm$^2$) to make the microneedle insert into the off-body skin, and followed by fixing the off-body skin of pig with the microneedles in a transdermal cup. 100 μl of the active ingredient gel of azelaic acid are added to a side of a drug delivery pool of the transdermal cup, and followed by automatically sampling with a fully automatic transdermal device. The drug content in a collection pool is analyzed by using a high-performance liquid chromatography device to calculate the cumulative transdermal transmittance of the drug. As shown in FIG. 9, the results show that when the hydrogel microneedle patch is used together with the commercially available azelaic acid gel preparation, the effective permeation of the drug could be achieved, and the cumulative permeation of azelaic acid reached 228 μg after continuous 10-hours applying, which can achieve good transdermal penetration of commercially available preparations.

Figure 10:
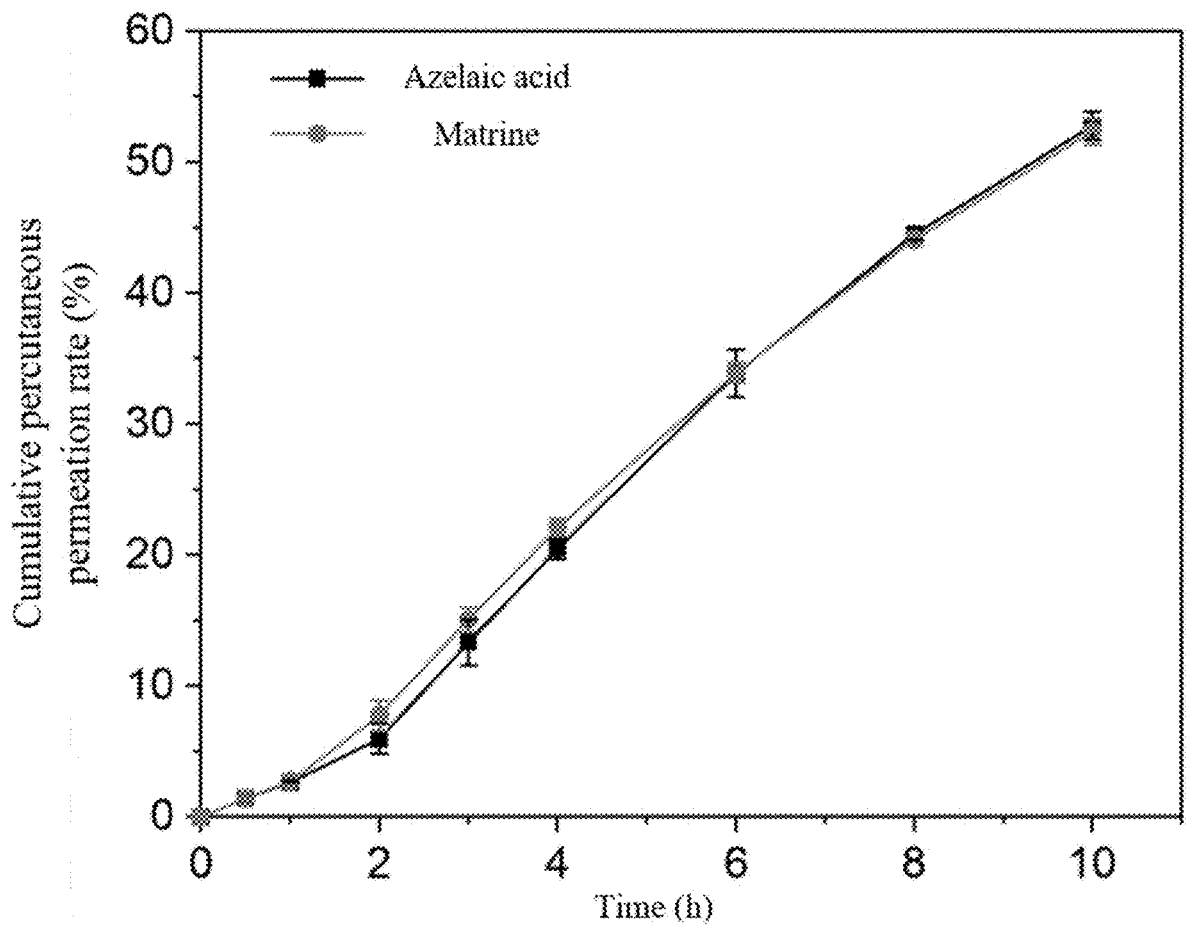
FIG. 10 illustrates cumulative percutaneous permeabilities of azelaic acid and matrine after applying the hydrogel microneedle patches respectively directly loaded with the azelaic acid and the matrine on skin surfaces in an embodiment 23 of the disclosure.

Embodiment 23 Percutaneous Permeability of Hydrogel Microneedle Patch Directly Loaded with Azelaic Acid and Matrine In the embodiment 23, a hydrogel microneedle patch is prepared through the following steps. A measuring cylinder is used to take 15.58 ml of purified water, 2.4 g of polyvinyl alcohol are add into the purified water to obtain a first mixed solution, then the first mixed solution is placed into an oven at a temperature of 90° C. to dissolve, thereby obtaining a polyvinyl alcohol solution. 2 g of polyvinyl pyrrolidone and 1.2 g of aqueous dispersion of acrylic resin (i.e., a copolymer of ethyl acrylate and methyl methacrylate with a molar ratio of 2:1) are added into the polyvinyl alcohol solution, followed by evenly stirring to obtain a mixed aqueous solution (i.e., a matrix solution of microneedle), in which a mass percentage of the polyvinyl alcohol in the mixed aqueous solution is 12 wt %, a mass percentage of the aqueous dispersion of acrylic resin in the mixed aqueous solution is of 6 wt % and a mass percentage of the polyvinyl pyrrolidone in the mixed aqueous solution is 10 wt %. Bubbles of the mixed aqueous solution are removed. An aqueous solution containing 1% mass content of azelaic acid and 1.3% mass content of matrine is prepared as an active ingredient solution, after the active ingredients are completely dissolved, the active ingredient solution and the mixed aqueous solution are mixed to obtain a microneedle loaded drug solution. The microneedle is prepared by the mold method, the microneedle loaded drug solution is added into a mold of the microneedle, and the hydrogel microneedle patch loaded with azelaic acid and matrine is obtained after the microneedles are dried to form a film. The microneedle is placed under an infrared radiation lamp at 70° C. for 2 minutes to promote microneedle cross-linking, then the hydrogel microneedle patch is applied to the cuticle side of the off-body skin of pig, the hydrogel microneedle is pressed for 20 seconds with a self-made needle inserter (with a pressure of 20 N/cm$^2$) to make the microneedle insert into the off-body skin, and followed by fixing the off-body skin of pig with the microneedles in a transdermal cup to automatically sample with a fully automatic transdermal device. The drug content in a collection pool is analyzed by using a high-performance liquid chromatography device to calculate the cumulative transdermal transmittance of the drug. As shown in FIG. 10, the results show that after continuous application for 10 hours, the cumulative permeation rates of azelaic acid and matrine could both reach over 50%, and the two drugs could maintain good synchronous release.

Figure 11:
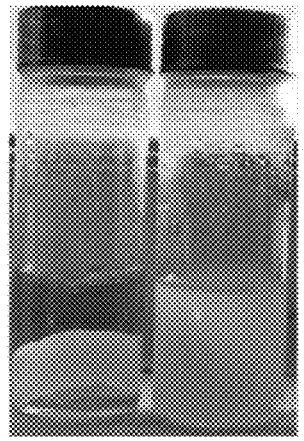
FIG. 11 illustrates a comparison diagram of a blank control group of microneedle (left) and a microneedle after acne puncture without culture medium solution (right) in an embodiment 24 of the disclosure.
Figure 12:
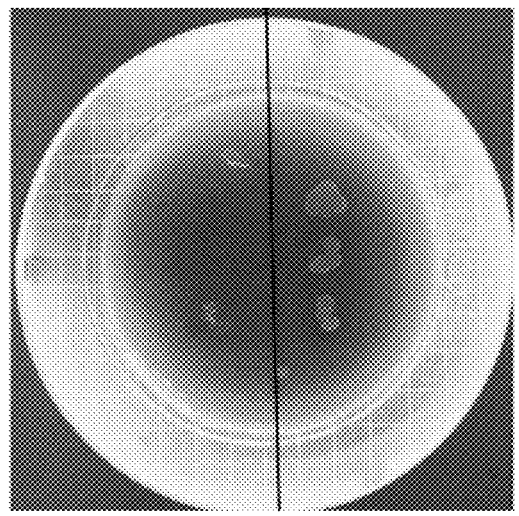
FIG. 12 illustrates a comparison diagram showing a bacteria growth situation of the blank control group of microneedle (left) and the microneedle after acne puncture (right) after the culture medium solution is added into each of the blank control group of microneedle and microneedle after acne puncture in the embodiment 24 of the disclosure.
Figure 13:
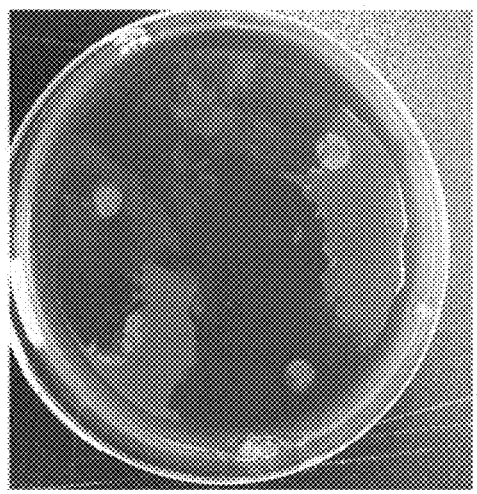
FIG. 13 illustrates a diagram of a positive control group of *Propionibacterium acnes* of in the embodiment 24 of the disclosure.

Embodiment 24 Extraction of *Propionibacterium acnes* from Skin Acne with Hydrogel Microneedle Patch In the embodiment 23, a hydrogel microneedle patch is prepared through the following steps. A measuring cylinder is used to take 16.4 ml of purified water, 4 g of polyvinyl alcohol are add into the purified water to obtain a first mixed solution, then the first mixed solution is placed into an oven at a temperature of 90° C. to dissolve, thereby obtaining a polyvinyl alcohol solution. 0.4 g of aqueous dispersion of acrylic resin (i.e., a copolymer of ethyl acrylate and methyl methacrylate with a molar ratio of 2:1) are added into the polyvinyl alcohol solution, followed by evenly stirring a mixed aqueous solution (i.e., a matrix solution of microneedle), in which a mass percentage of the polyvinyl alcohol in the mixed aqueous solution is 20 wt %, and a mass percentage of the aqueous dispersion of acrylic resin in the mixed aqueous solution is of 2 wt %. Bubbles of the mixed aqueous solution are removed. The microneedle is prepared by the mold method, the mixed aqueous solution is added into a mold of the microneedle, the hydrogel microneedle patch is obtained after the microneedles are dried to form a film, and the hydrogel microneedle patch is placed under a ultraviolet lamp for overnight radiation sterilization. An alcohol swab is used to disinfect the acne area on the face of a volunteer with acne, then the sterile hydrogel microneedle patch is used to be sticked into the skin of the acne area for applying the sterile hydrogel microneedle patch for 3 minutes, followed by taking off the sterile hydrogel microneedle patch, and putting the microneedle into a sterile fluid thioglycollate medium II prepared in advance. Simultaneously, a piece of hydrogel microneedle not in contact with the skin is taken as a blank control, and the hydrogel microneedle not in contact with the skin is directly put into the sterile fluid thioglycollate medium II. Two sets of culture medium solutions of hydrogel microneedle being in and not in contact with the skin are placed in an anaerobic environment at 37° C. to incubate for 72 hours, followed by taking out the two sets of culture medium solutions and observing whether there is bacterial growth situation in the culture medium in both bottles. A small amount of culture medium from each bottle is taken and added dropwise to sterile Columbia blood agar solid culture medium, followed by placing in an anaerobic environment at 37° C. to incubate for 72 hours. After the incubating, the culture mediums are taken out to observe the growth of colonies on the culture plate, followed by comparing *Propionibacterium acnes* extracted from the skin with the positive control purchased *Propionibacterium acnes* strain to determine whether acne bacteria have been successfully extracted from the skin. As shown in FIGS. 11-13, FIG. 11 illustrates a comparison diagram of a blank control group of microneedle (left) and a microneedle after acne puncture without culture medium solution (right), FIG. 12 illustrates a comparison diagram showing a bacteria growth situation of the blank control group of microneedle (left) and the microneedle after acne puncture (right) after the culture medium solution is added into each of the blank control group of microneedle and microneedle after acne puncture, and FIG. 12 illustrates a comparison diagram showing a bacteria growth situation of the blank control group of microneedle (left) and the microneedle after acne puncture (right) after the culture medium solution is added into each of the blank control group of microneedle and microneedle after acne puncture. The results show that the hydrogel microneedle has obvious turbidity in the sterile fluid thioglycollate medium II after applying it on skin acne, indicating that there is bacterial growth. In contrast, the culture medium of the hydrogel microneedle group that is not in contact with the skin is still clear, and no bacteria existed. In addition, after inoculation into the blood agar culture dish, it is found that the hydrogel microneedle group applying on skin acne grew white colonies on the agar, and the colony surface is smooth, which is consistent with the colony morphology of the positive control group of *Propionibacterium acnes*, indicating that the hydrogel microneedle patch could be used for the extraction of *Propionibacterium acnes* in skin acne.

Apparently, the above embodiments of the disclosure are only for the purpose of clearly illustrating the embodiments of the disclosure, and are not a limitation on the embodiments of the disclosure. For those skilled in the art, other different forms of variations or variations can be made on the basis of the above explanation. Here, it is not possible to exhaustively list all embodiments. Any obvious changes or variations derived from the technical solutions of the disclosure are still within the scope of protection of the disclosure.

What is claimed is:

1. A hydrogel microneedle patch based on a three-dimensional framework structure, the hydrogel microneedle patch comprising: a hydrogel microneedle;
    wherein a raw material of the hydrogel microneedle comprises a polyvinyl alcohol and an aqueous dispersion of an acrylic resin;
    wherein the hydrogel microneedle is obtained by uniformly mixing and molding of the aqueous dispersion of the acrylic resin and the polyvinyl alcohol;
    wherein in the hydrogel microneedle patch, the aqueous dispersion of the acrylic resin is configured to, as the three-dimensional framework structure, enclose a gel formed by the polyvinyl alcohol;
    wherein the hydrogel microneedle further comprises a pore-forming agent, and the pore-forming agent is located in the polyvinyl alcohol or the aqueous dispersion of the acrylic resin;
    wherein a mass percentage of the pore-forming agent in the hydrogel microneedle is in a range of 0.1-10 weight percent (wt %); and
    wherein in the aqueous dispersion of the acrylic resin, the acrylic resin comprises one or more selected from the group consisting of a copolymer of ethyl acrylate and methyl methacrylate with a molar ratio of 2:1, a copolymer of methacrylic acid, methyl acrylate and methyl methacrylate with a molar ratio of 1:1:1, a copolymer of ethyl acrylate, methyl methacrylate and methacryloxyethyltrimethyl ammonium chloride with a molar ratio of 1:2:0.1, a copolymer of ethyl acrylate, methyl methacrylate and methacryloxyethyltrimethyl ammonium chloride with a molar ratio of 1:2:0.2, and a copolymer of methacrylic acid and ethyl acrylate with a molar ratio of 1:1.

2. The hydrogel microneedle patch as claimed in claim 1, wherein the pore-forming agent comprises one or more selected from the group consisting of polyvinylpyrrolidone, calcium phosphate dibasic, sodium bicarbonate, sodium carbonate, trehalose, fructose, sorbitol, mannitol, xylitol, galactose, magnesium chloride, calcium chloride and zinc chloride.

3. A hydrogel microneedle patch based on a three-dimensional framework structure, the hydrogel microneedle patch comprising: a hydrogel microneedle;
    wherein a raw material of the hydrogel microneedle comprises a polyvinyl alcohol and an aqueous dispersion of an acrylic resin;
    wherein the hydrogel microneedle is obtained by uniformly mixing and molding of the aqueous dispersion of the acrylic resin and the polyvinyl alcohol;
    wherein in the hydrogel microneedle patch, the aqueous dispersion of the acrylic resin is configured to, as the three-dimensional framework structure, enclose a gel formed by the polyvinyl alcohol; and
    wherein in the aqueous dispersion of the acrylic resin, the acrylic resin comprises one or more selected from the group consisting of a copolymer of ethyl acrylate and methyl methacrylate with a molar ratio of 2:1, a copolymer of methacrylic acid, methyl acrylate and methyl methacrylate with a molar ratio of 1:1:1, a copolymer of ethyl acrylate, methyl methacrylate and methacryloxyethyltrimethyl ammonium chloride with a molar ratio of 1:2:0.1, a copolymer of ethyl acrylate, methyl methacrylate and methacryloxyethyltrimethyl ammonium chloride with a molar ratio of 1:2:0.2, and a copolymer of methacrylic acid and ethyl acrylate with a molar ratio of 1:1.

* * * * *